(12) United States Patent
Grauwinkel et al.

(10) Patent No.: US 12,702,819 B2
(45) Date of Patent: Aug. 11, 2026

(54) BLOOD PUMP

(71) Applicant: Abiomed Europe GmbH, Aachen (DE)

(72) Inventors: Marius Grauwinkel, Aachen (DE); Wolfgang Kerkhoffs, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 907 days.

(21) Appl. No.: 17/439,212

(22) PCT Filed: Mar. 16, 2020

(86) PCT No.: PCT/EP2020/057158
§ 371 (c)(1),
(2) Date: Sep. 14, 2021

(87) PCT Pub. No.: WO2020/187860
PCT Pub. Date: Sep. 24, 2020

(65) Prior Publication Data

US 2022/0161020 A1 May 26, 2022

(30) Foreign Application Priority Data

Mar. 19, 2019 (EP) .................................... 19163662

(51) Int. Cl.
*A61M 60/135* (2021.01)
*A61M 60/13* (2021.01)
(Continued)

(52) U.S. Cl.
CPC .......... *A61M 60/221* (2021.01); *A61M 60/13* (2021.01); *A61M 60/139* (2021.01);
(Continued)

(58) Field of Classification Search
CPC ............................ A61M 60/422; A61M 60/82
See application file for complete search history.

(56) References Cited

U.S. PATENT DOCUMENTS

2003/0111926 A1* 6/2003 Decristofaro .......... B82Y 25/00 310/216.106
2009/0112312 A1* 4/2009 LaRose ............... A61M 60/861 417/423.1
(Continued)

FOREIGN PATENT DOCUMENTS

CN 108883216 A 11/2018
EP 3069738 A1 9/2016
(Continued)

OTHER PUBLICATIONS

Office Action from corresponding Chinese Patent Application No. 202080022899.0 dated Jul. 28, 2023 (22 pp.).
(Continued)

*Primary Examiner* — Michael J D'Abreu
(74) *Attorney, Agent, or Firm* — BOTOS CHURCHILL IP LAW LLP

(57) ABSTRACT

This invention concerns an intravascular blood pump for percutaneous insertion into a patient's blood vessel. The blood pump comprises a pump casing having a blood flow inlet and a blood flow outlet, an impeller arranged in said pump casing so as to be rotatable about an axis of rotation. The impeller has blades sized and shaped for conveying blood from the blood flow inlet to the blood flow outlet. The blood pump comprises a drive unit for rotating the impeller, the drive unit comprising a magnetic core including a plurality of posts arranged about the axis of rotation and a back plate connecting the posts and extending between the posts in an intermediate area. A coil winding is disposed around each of the posts. The coil windings are controllable so as to create a rotating magnetic field, wherein the impeller comprises a magnetic structure arranged to interact with the rotating magnetic field so as to cause rotation of the impeller. A material of at least a portion of at least one of the posts is integral with a material of the intermediate area of the back
(Continued)

plate. Further, the invention concerns a method of manufacturing a magnetic core and a method of manufacturing an intravascular blood pump.

17 Claims, 6 Drawing Sheets

(51) Int. Cl.

| | |
|---|---|
| ***A61M 60/139*** | (2021.01) |
| ***A61M 60/216*** | (2021.01) |
| ***A61M 60/221*** | (2021.01) |
| ***A61M 60/237*** | (2021.01) |
| ***A61M 60/422*** | (2021.01) |
| ***A61M 60/508*** | (2021.01) |
| ***A61M 60/804*** | (2021.01) |
| ***A61M 60/818*** | (2021.01) |
| ***A61M 60/82*** | (2021.01) |
| ***B23H 1/00*** | (2006.01) |

(52) U.S. Cl.
CPC ........ *A61M 60/216* (2021.01); *A61M 60/237* (2021.01); *A61M 60/422* (2021.01); *A61M 60/508* (2021.01); *A61M 60/804* (2021.01); *A61M 60/818* (2021.01); *A61M 60/82* (2021.01); *B23H 1/00* (2013.01); *A61M 2207/00* (2013.01)

(56) References Cited

U.S. PATENT DOCUMENTS

| | | | | |
|---|---|---|---|---|
| 2011/0084569 | A1* | 4/2011 | Asano .................... | H02K 1/148 310/216.058 |
| 2011/0238172 | A1 | 9/2011 | Akdis | |
| 2017/0302145 | A1* | 10/2017 | Holenstein ............ | B01F 33/453 |

FOREIGN PATENT DOCUMENTS

| | | | |
|---|---|---|---|
| EP | 3222301 | A1 | 9/2017 |
| JP | 2011066979 | A | 3/2011 |
| JP | 2012189072 | A | 10/2012 |
| JP | 2014241701 | A | 12/2014 |
| JP | 2017169296 | A | 9/2017 |
| JP | 2017192295 | A | 10/2017 |
| KR | 20100134729 | A | 12/2010 |
| KR | 20180123708 | A | 11/2018 |
| WO | 2014035354 | A1 | 3/2014 |
| WO | 2016056294 | A1 | 4/2016 |
| WO | 2017162619 | A1 | 9/2017 |
| WO | 2018187576 | A2 | 10/2018 |

OTHER PUBLICATIONS

First Office Action for corresponding Indian Application No. 202117041163 dated Aug. 30, 2023 (6 pages).
Extended European Search Report for European Application No. 19163662.0 dated Sep. 24, 2019 (5 pages).
International Search Report and Written Opinion for International Application No. PCT/EP2020/057158 dated Jun. 3, 2020 (12 pages).
Office Action from corresponding Japanese Patent Application No. 2021-556254 dated Dec. 19, 2023 (8 pp.).
Office Action from corresponding Chinese Patent Application No. 202080022899.0 dated Apr. 23, 2024 (21 pp.).
Office Action from corresponding Korean Patent Application No. 10-2021-7033648 dated Apr. 24, 2025 (12 pp.).
Office Action from New Zealand Patent Application No. 779319 dated Apr. 26, 2024 (4 pp.).
Extended European Search Report for European Application No. 26153883.9 dated Apr. 16, 2026 (9 pp.).

* cited by examiner 1
2
3
4
6
10
11
12
13
14
21
22
22
23
24
25
26
31
31
32
37
40
40
44
44
50
420

400
450
LA
10
DL
LA
450
85
50
401
401
40
40
4
44
44
420
420
15
32
11
37
31
31
3
12

FIG 5A
141
171
172
FIG 5B
141
171
172
FIG 5C
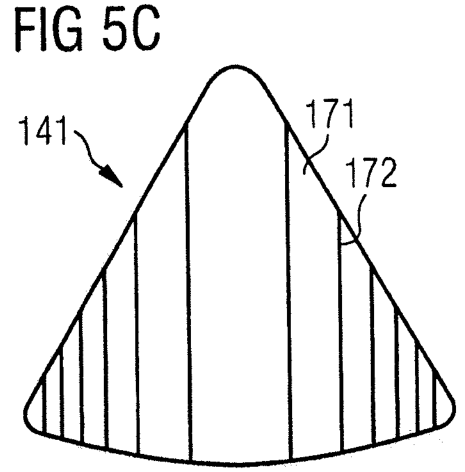
FIG 5D
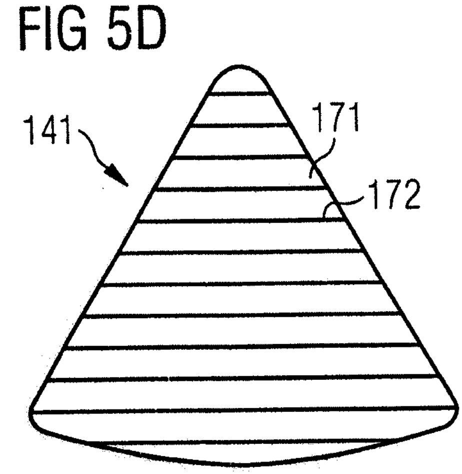

BLOOD PUMP

CROSS-REFERENCE TO RELATED APPLICATIONS

The present application is a national phase entry under 35 U.S.C. § 371 of International Application No. PCT/EP2020/057158, filed Mar. 16, 2020, published as International Publication No. WO 2020/187860 A1, which claims the benefit of the filing date of European Patent Application No. 19163662.0 filed Mar. 19, 2019, the disclosures of which are hereby incorporated herein by reference.

This invention relates to a blood pump, in particular an intravascular blood pump for percutaneous insertion into a patient's blood vessel, to support a blood flow in a patient's blood vessel. The blood pump has an improved drive unit.

BACKGROUND OF INVENTION

Blood pumps of different types are known, such as axial blood pumps, centrifugal (i.e. radial) blood pumps or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet connected by a passage. In order to cause a blood flow along the passage from the blood flow inlet to the blood flow outlet, an impeller or rotor is rotatably supported within the pump casing, with the impeller being provided with blades for conveying blood.

Blood pumps are typically driven by a drive unit, which can be an electric motor. For instance, US 2011/0238172 A1 discloses extracorporeal blood pumps having an impeller which may be magnetically coupled to an electric motor. The impeller comprises magnets which are disposed adjacent to magnets in the electric motor. Due to attracting forces between the magnets in the impeller and in the motor, rotation of the motor is transmitted to the impeller. In order to reduce the number of rotating parts, it is also known from US 2011/0238172 A1 to utilize a rotating magnetic field, with the drive unit having a plurality of static posts arranged about the axis of rotation, and each post carrying a wire coil winding and acting as a magnetic core. A control unit sequentially supplies a voltage to the coil windings to create the rotating magnetic field. In order to provide a sufficiently strong magnetic coupling, the magnetic forces have to be high enough, which can be achieved by a sufficiently high current supplied to the drive unit or by providing large magnets, which, however, leads to a large overall diameter of the blood pump.

EP 3222301 B1 discloses a blood pump, in particular an intravascular blood pump, having a magnetic coupling between the drive unit and the impeller, wherein the blood pump has a compact design, and in particular a high ratio of pumping power to size of the pump, resulting in sufficiently small outer dimensions to allow the blood pump to be inserted transvascularly, transvenously, transarterially or transvalvularly or being even smaller for reasons of handling and convenience.

More specifically, the blood pump in EP 3222301 B1 comprises a pump casing with a blood flow inlet and a blood flow outlet, an impeller and a drive unit for rotating the impeller. By rotation of the impeller about an axis of rotation and inside of the pump casing, blood can be conveyed from the blood flow inlet to the blood flow outlet by blades of the impeller. The drive unit comprises a magnetic core which comprises a plurality of preferably six posts and a back plate connecting rear ends of the posts to act as a yoke. The posts are arranged in a circle around the axis of rotation, as seen in a plane which is perpendicular to the axis of rotation, wherein each of the posts has a longitudinal axis, which is preferably parallel to said axis of rotation. The back plate has through openings in each of which a rear end of the posts is received in a form-fitting manner such that the end surface of the rear end of each post is flush with a rear surface of the back plate. This way, a magnetic connection between the posts and the back plate is generated between a circumference of the posts and an inner contour of the openings of the back plate. The posts each have a coil winding disposed around the post. In order to generate a rotating magnetic field for driving the impeller, the coil windings can be controlled in a coherent manner. The impeller comprises a magnetic structure in the form of a magnet which is arranged to interact with the rotating magnetic field such that the impeller follows its rotation.

It is an object of the invention to improve the magnetic flux in the magnetic core.

SUMMARY OF THE INVENTION

The blood pump of the present invention corresponds to the afore-mentioned blood pump. Accordingly, it may be an axial blood pump or a diagonal blood pump, which pumps partly axially and partly radially, (the diameter of pure centrifugal blood pumps is usually too large for intravascular applications). However, according to one aspect of the invention, material of at least a portion of at least one of the posts of the magnetic core is integral with the material of an intermediate area of the magnetic core's back plate wherein the intermediate area of the back plate is an area of the back plate situated between the posts. Preferably, all posts are connected integrally to the back plate in this way. In other words, at least one post and the back plate, preferably the entire magnetic core, can be made of a single block of material, hereinafter also referred to as monoblock. An advantage of such a magnetic core is that magnetic resistance at the transition between the posts and the back plate is minimized and, thus, magnetic flux is improved. Further, a good mechanical rigidity of the transition between the posts and the back plate can be achieved.

Each of the posts has a longitudinal axis, which may be parallel to the axis of rotation. Preferably, the magnetic core comprises a discontinuous soft magnetic material. More preferably, the soft magnetic material of the magnetic core is discontinuous in cross-section transverse, preferably perpendicular, to the longitudinal axis of the posts. In other words, the soft magnetic material of the posts is discontinuous in cross-section transverse, preferably perpendicular, to a direction of magnetic flux caused by the respective coil winding in the post. By dividing or interrupting the soft magnetic material in cross section, eddy currents in the posts can be reduced or avoided, such that heat generation and energy consumption can be reduced. Reducing energy consumption is particularly useful for long term applications of the blood pump, in which it is desirable that the blood pump is battery-powered to provide mobility for the patient. Also in long term applications, the blood pump may be operated without purge, which is only possible if heat generation is low.

"Discontinuous" in the sense of the present document means that the soft magnetic material as seen in any cross-section transverse to e.g. the longitudinal axis of the post is interrupted, separated, intersected or the like by means of insulating material or other materials or gaps in order to form strictly separated areas of soft magnetic material or areas that are interrupted but connected at a different location.

Providing a discontinuous soft magnetic material in cross-sectional planes transverse to the direction of the magnetic flux reduces eddy currents and thus heat generation and energy consumption as explained above. In order not to substantially weaken the magnetic field compared to a continuous or full body (i.e. solid) soft magnetic material, the total amount of soft magnetic material is to be maximized while minimizing the continuous areas of soft magnetic material. This can be achieved for example by providing the soft magnetic material in the form of a plurality of sheets of soft magnetic material, such as electric steel. In particular, the sheets may form a stack of sheets. The sheets are preferably electrically insulated from each other, e.g. by providing adhesive, lacquer, baking enamel or the like between adjacent ones of the sheets. Such arrangement can be denoted as "slotted". Compared to a full body soft magnetic material, the amount of soft magnetic material is recued only little and the amount of insulating material is kept small, such that the magnetic field caused by a slotted post is substantially the same as the magnetic field caused by a solid post. In other words, while heat generation and energy consumption can be reduced significantly, the loss in magnetic field caused by the insulating material is insignificant.

The sheets preferably extend substantially parallel to the longitudinal axis of the respective post. In other words, the sheets may extend substantially parallel to the direction of the magnetic flux, such that the posts are discontinuous in cross-section transverse or perpendicular to the direction of the magnetic flux. It will be appreciated that the sheets may extend at an angle relative to the longitudinal axis of the respective post as long as the soft magnetic material is discontinuous in cross-section transverse to the longitudinal axis. The sheets preferably have a thickness in the range of 25 μm to 1 mm, more preferably 50 μm to about 450 μm, for instance 200 μm.

Particularly, the areas of a certain type of material, such as the sheets of soft magnetic material, may extend in both the posts and the back plate. Although the material is discontinuous, the magnetic core can be made of a single block of such a material. The extension of such areas of a certain type of material is not interrupted by the transition between the posts and the back plate but continuous integrally from the posts into an intermediate area of the back plate located between the posts.

It is generally known to provide slotted soft magnetic material, such as electrical steel, in electric motors to avoid or reduce eddy currents. However, this technology has been applied for large devices in which the sheets usually have a thickness in the range of about 500 μm or higher. In small applications, such as the blood pump of the present invention, in which one of the posts usually has a diameter in said order of magnitude, and in which the power input is relatively low (e.g. up to 20 watts (W)), eddy currents and the associated problems were not expected. Surprisingly, despite the small diameter of the posts, eddy currents and thus heat generation and energy consumption can be reduced by providing slotted posts. This is advantageous for operation of the blood pump, which may be operated at a high speed of up to 50,000 rpm (revolutions per minute).

It will be appreciated that other arrangements than the aforementioned slotted arrangement to provide a discontinuous soft magnetic material in the posts may be possible. For instance, instead of a plurality of sheets, a plurality of wires, fibers, posts or other elongate elements can be provided to form each of the posts of the drive unit. The wires or the like may be provided in the form of a bundle with the wires being electrically insulated from each other, e.g. by means of a coating surrounding each wire or an insulating matrix in which the wires are embedded, and may have various cross-sectional shapes, such as circular, round, rectangular, square, polygonal etc. Likewise, particles of a soft magnetic material, wire wool or other sponge-like or porous structures of soft magnetic material can be provided, in which the space between the areas of soft magnetic material comprises an electrically insulating material, such as an adhesive, lacquer, polymer matrix or the like. A porous and, thus, discontinuous structure of soft magnetic material may also be formed by a sintered material or pressed material. In such structure, an additional insulating material may be omitted because insulating layers may be formed automatically by oxide layers resulting from oxidation of the soft magnetic material by exposure to air.

While the sheets or other structures of soft magnetic material may be formed uniformly, i.e. the sheets within one of the posts or all posts may have the same thickness or wires may have the same diameter, a non-uniform arrangement can be provided. For instance, the sheets may have a varying thickness or the wires may have a varying diameter. More specifically, in particular with regards to a stack of sheets, one or more central sheets may have a larger thickness, while adjacent sheets towards the ends of the stack may have a smaller thickness, i.e. the thickness of the sheets decreases from the center towards the ends of the stack, i.e. towards the outermost sheets of the stack. Similarly, one or more central wires in a bundle of wires may have a larger diameter, while wires at the edge of the post may have a smaller diameter, i.e. the diameter of the wires may decrease from the center towards the edges of the bundle, i.e. towards the outermost wires of the bundle. Providing a larger continuous area of soft magnetic material in the center of the post with respect to a cross-section transverse to its longitudinal axis, i.e. relatively thick sheets or wires in the center, may be advantageous because this may enhance the magnetic flux through the center along the longitudinal axis of each post, and eddy currents in the center are less relevant than eddy currents at the sides of the posts. In other words, such arrangement may be advantageous because eddy currents in the side regions of the posts are more critical and can be reduced by thin sheets or wires in the side regions.

The diameter of the back plate may be in the range of 3 mm to 9 mm, such as 5 mm or 6 mm to 7 mm. The thickness of the back plate may be in the range of 0.5 mm to 2.5 mm, such as 1.5 mm. The outer diameter of the blood pump may be in the range of 4 mm to 10 mm, preferably 7 mm. The outer diameter of the arrangement of the plurality of posts may be in the range of 3 mm to 8 mm, such as 4 mm to 7.5 mm, preferably 6.5 mm.

As stated above, the posts are made of a soft magnetic material such as electrical steel (magnetic steel). The posts and the back plate may be made of the same material. Preferably, the drive unit, including the posts and the back plate, is made of cobalt steel. The use of the cobalt steel contributes to reducing the pump size, in particular the diameter. With the highest magnetic permeability and highest magnetic saturation flux density among all magnetic steels, cobalt steel produces the most magnetic flux for the same amount of material used.

The dimensions of the posts, in particular length and cross-sectional area, may vary and depend on various factors. In contrast to the dimensions of the blood pump, e.g. the outer diameter, which depend on the application of the blood pump, the dimensions of the posts are determined by electromagnetic properties, which are adjusted to achieve a desired performance of the drive unit. One of the factors is the flux density to be achieved through the smallest cross-sectional area of the posts. The smaller the cross-sectional area, the higher is the necessary current to achieve the desired magnetic flux. A higher current, however, generates more heat in the wire of the coil due to electrical resistance. That means, although "thin" posts are preferred to reduce the overall size, this would require high current and, thus, result in undesired heat. The heat generated in the wire also depends on the length and diameter of the wire used for the coil windings. A short wire length and a large wire diameter are preferred in order to minimize the winding loss (referred to as "copper loss" or "copper power loss" if copper wires are used, which is usually the case). In other words, if the wire diameter is small, more heat is generated compared to a thicker wire at the same current, a preferred wire diameter being e.g. 0.05 mm to 0.2 mm, such as 0.1 mm. Further factors influencing the post dimensions and the performance of the drive unit are the number of windings of the coil and the outer diameter of the windings, i.e. the post including the windings. A large number of windings may be arranged in more than one layer around each post, for instance, two or three layers may be provided. However, the higher the number of layers, the more heat will be generated due to the increased length of the wire in the outer layers having a larger winding diameter. The increased length of the wire may generate more heat due to the higher resistance of a long wire compared to a shorter one. Thus, a single layer of windings with a small winding diameter would be preferred.

A typical number of windings, which in turn depends on the length of the post, may be about 50 to about 150, e.g. 56 or 132. Independent of the number of windings, the coil windings are made of an electrically conductive material, in particular metal, such as copper or silver. Silver may be preferred to copper because silver has an electrical resistance which is about 5% less than the electrical resistance of copper.

Preferably, the magnetic core comprises one or more welds. The welds can be arranged on an outer surface of the magnetic core, which is particularly accessible for e.g. laser welding. The welds bridge discontinuities regarding electric conductivity in the soft magnetic material and, thus, electrically connect at least two sheets of soft magnetic material. The welds also add mechanical stability to the discontinuous soft magnetic material.

One or more welds can be arranged on a surface of the back plate opposite to the posts. They can be generated by laser welding. In case that a material made of laminated sheets is used, the welds preferably bridge neighboring soft magnetic sheets obliquely or transversely.

In a further aspect of the invention, a method of manufacturing a magnetic core for a drive unit of an intravascular blood pump is proposed. The magnetic core has an axis of rotation and includes a plurality of posts which are arranged about the axis of rotation and a back plate that connects the posts. The method comprises the steps of providing a monoblock of magnetically conductive material and cutting slots into the monoblock so as to create the posts such that they are arranged about the axis of rotation and the back plate, so that the back plate forms an integral piece with the posts. As pointed out above, an advantage of such manufacturing is to produce a magnetic core with reduced magnetic resistance.

At least one slot, preferably all slots which oppose each other relative to the axis of rotation, may be produced by cutting through the axis of rotation of the magnetic core. Then, an even distribution of the posts about the axis of rotation can be achieved easily.

Preferably, the slots are cut so that the posts all have an identical length. The slots are particularly cut such that the back plate has a thickness which is smaller than a maximum cross-sectional dimension of the posts transverse to a longitudinal axis thereof.

It is preferred to cut the slots using electric discharge machining, especially wire electric discharge machining, or electrochemical machining. These methods apply only little forces on the material to be machined and are therefore particularly advantageous for machining the discontinuous material.

In a further aspect of the invention, a method of manufacturing a blood pump is proposed. The blood pump comprises a drive unit with a magnetic core, wherein the magnetic core is manufactured in the manner as described before.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings:

FIGS. 5A to 5J show cross-sections through posts according to various embodiments.

DETAILED DESCRIPTION

Figure 1:
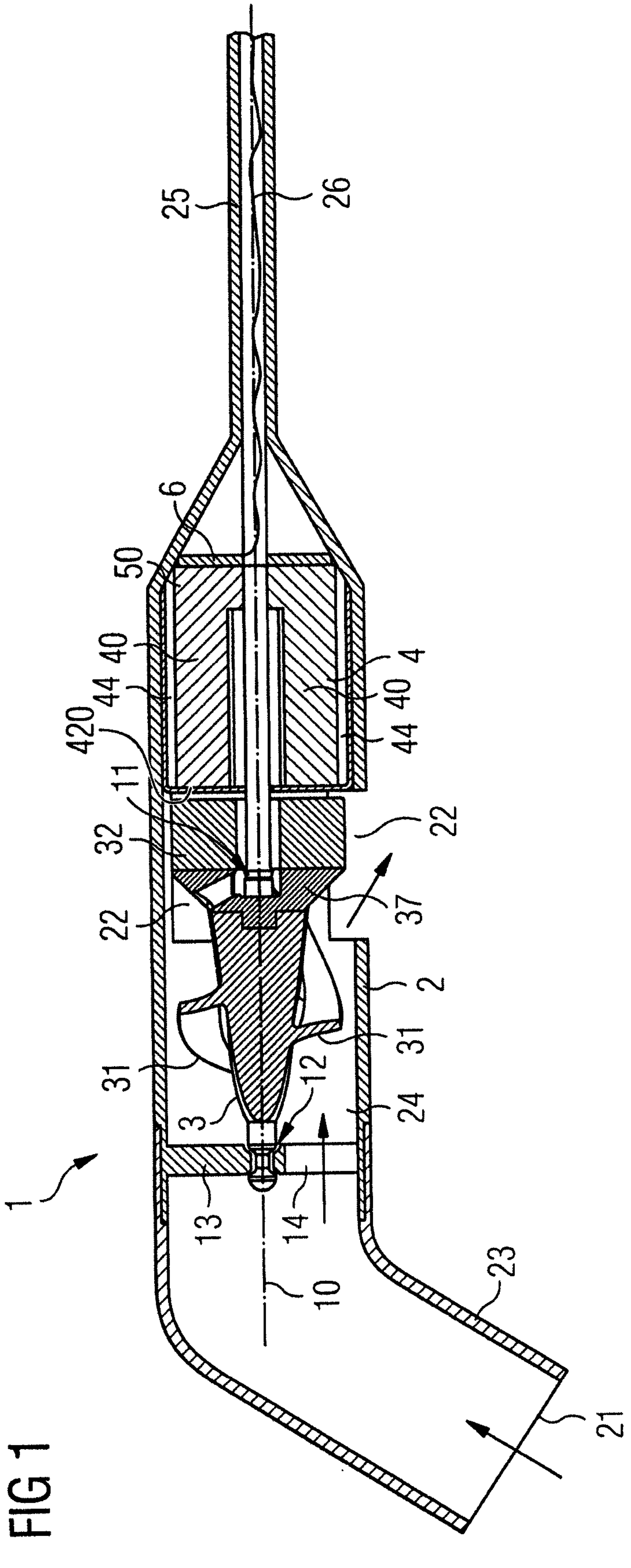
FIG. 1 shows a cross-sectional view of a blood pump.

Referring to FIG. 1, a cross-sectional view of a blood pump 1 is illustrated. The blood pump 1 comprises a pump casing 2 with a blood flow inlet 21 and a blood flow outlet 22. The blood pump 1 is designed as an intravascular pump, also called a catheter pump, and is deployed into a patient's blood vessel by means of a catheter 25. The blood flow inlet 21 is at the end of a flexible cannula 23 which may be placed through a heart valve, such as the aortic valve, during use. The blood flow outlet 22 is located in a side surface of the pump casing 2 and may be placed in a heart vessel, such as the aorta. The blood pump 1 is electrically connected with an electric line 26 extending through the catheter 25 for supplying the blood pump 1 with electric power in order to drive the pump 1 by means of a drive unit 4, as explained in more detail below.

If the blood pump 1 is intended to be used in long term applications, i.e. in situations in which the blood pump 1 is implanted into the patient for several weeks or even months, electric power is preferably supplied by means of a battery. This allows a patient to be mobile because the patient is not connected to a base station by means of cables. The battery can be carried by the patient and may supply electric energy to the blood pump 1, e.g. wirelessly.

The blood is conveyed along a passage 24 connecting the blood flow inlet 21 and the blood flow outlet 22 (blood flow indicated by arrows). An impeller 3 is provided for conveying blood along the passage 24 and is mounted to be rotatable about an axis of rotation 10 within the pump casing 2 by means of a first bearing 11 and a second bearing 12. The axis of rotation 10 is preferably the longitudinal axis of the impeller 3. Both bearings 11, 12 are contact-type bearings in this embodiment. At least one of the bearings 11, 12 could be a non-contact-type bearing, however, such as a magnetic or hydrodynamic bearing. The first bearing 11 is a pivot bearing having spherical bearing surfaces that allow for rotational movement as well as pivoting movement to some degree. A pin 15 is provided, forming one of the bearing surfaces. The second bearing 12 is disposed in a supporting member 13 to stabilize the rotation of the impeller 3, the supporting member 13 having at least one opening 14 for the blood flow. Blades 31 are provided on the impeller 3 for conveying blood once the impeller 3 rotates. Rotation of the impeller 3 is caused by the drive unit 4 which is magnetically coupled to a magnet 32 at an end portion of the impeller 3. The illustrated blood pump 1 is a mixed-type blood pump, with the major direction of flow being axial. It will be appreciated that the blood pump 1 could also be a purely axial blood pump, depending on the arrangement of the impeller 3, in particular the blades 31.

The blood pump 1 comprises the impeller 3 and the drive unit 4. The drive unit 4 comprises a plurality of posts 40, such as six posts 40, only two of which are visible in the cross-sectional view of FIG. 1. The posts 40 are arranged parallel to the axis of rotation 10, more specifically, a longitudinal axis of each of the posts 40 is parallel to the axis of rotation 10. One end of the posts 42 is disposed adjacent to the impeller. Coil windings 44 are arranged about the posts 40. The coil windings 44 are sequentially controlled by a control to create a rotating magnetic field. A part of the control unit is the printed circuit board 6 which is connected to the electric line 26. The impeller has a magnet 32, which is formed as a multiple piece magnet in this embodiment. The magnet 32 is disposed at the end of the impeller 3 facing the drive unit 4. The magnet 32 is arranged to interact with the rotating magnetic field so as to cause rotation of the impeller 3 about the axis of rotation 10.

In order to close the magnetic flux path, a back plate 50 is located at the end of the posts 40 opposite the impeller-side of the posts. The posts 40 act as a magnetic core and are made of a suitable material, in particular a soft magnetic material, such as steel or a suitable alloy, in particular cobalt steel. Likewise, the back plate 50 is made of a suitable soft magnetic material, such as cobalt steel. The back plate 50 enhances the magnetic flux, which allows for reduction of the overall diameter of the blood pump 1, which is important for intravascular blood pumps. For the same purpose, a yoke 37, i.e. an additional impeller back plate, is provided in the impeller 3 at a side of the magnet 32 facing away from the drive unit 4. The yoke 37 in this embodiment has a conical shape in order to guide the blood flow along the impeller 3. The yoke 37 may be made of cobalt steel, too. One or more wash-out channels that extend towards the central bearing 11 may be formed in the yoke 37 or the magnet 32.

Figure 2:
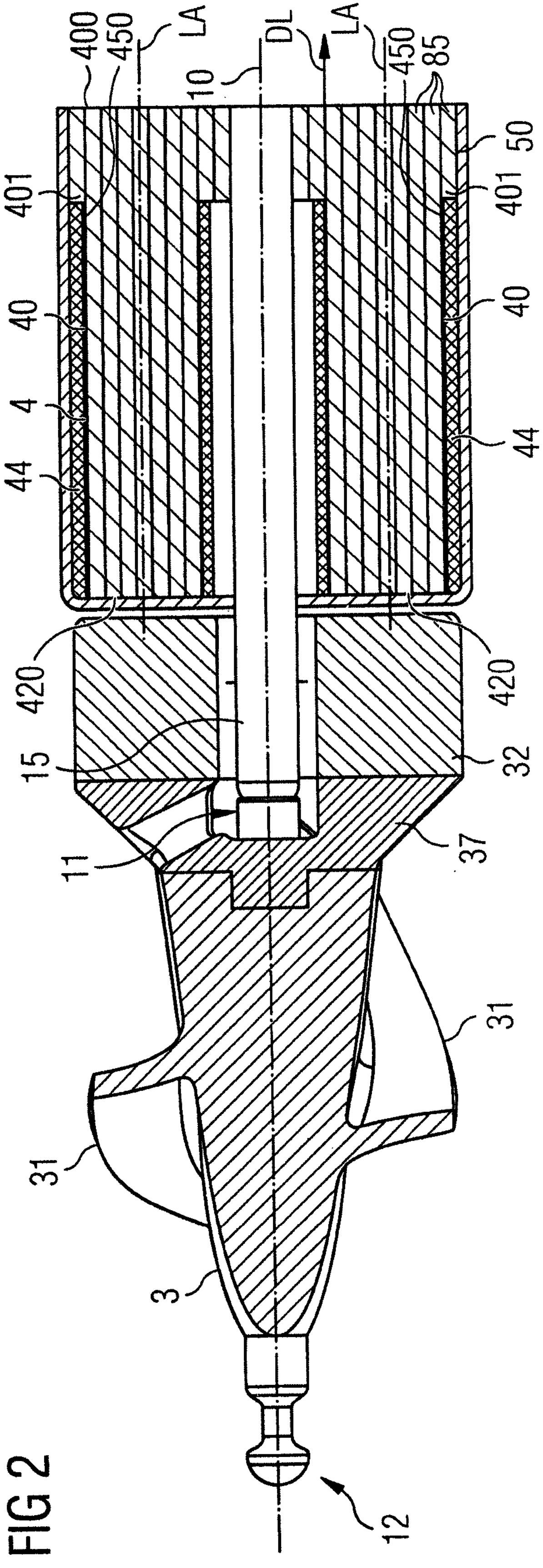
FIG. 2 shows a cross-sectional view of a preferred embodiment of a drive unit-impeller-arrangement.

FIG. 2 shows a cross-sectional view of a preferred embodiment of a drive unit-impeller-arrangement for the blood pump according to FIG. 1. As can be seen in FIG. 2, the impeller-side ends 420 of the posts 40 do not extend radially over the windings 44. Rather, the cross section of the posts 40 is constant in the direction of a longitudinal axis LA of the posts 40. It is thus avoided that the posts 40 come close to each other, as this could cause a partial magnetic short-circuit with the result of a reduced power of the electric motor of the blood pump.

The drive unit according to FIG. 2 may comprise at least two, at least three, at least four, at least five or preferably six posts 40. Higher numbers of posts 40, such as nine or twelve, may be possible. Due to the cross-sectional view, only two posts 40 are visible. The posts 40 and the back plate 50 form a magnetic core 400 of the drive unit 4 which may have a diameter of less than 10 mm.

The magnetic core 400 comprises the magnetic components of the drive unit 4, which are the posts 40 and the back plate 50, as one single piece or monoblock. The monoblock consists of discontinuous soft magnetic material that is discontinuous in regard of electric conductivity. The discontinuous soft magnetic material comprises a plurality of sheets 85 which are made of a ferromagnetic material and which are laminated to each other. A direction of lamination is arranged in direction of the longitudinal axis LA of the posts 40 and marked by an arrow DL. As shown, the posts 40 are arranged in parallel to the axis of rotation 10.

The coil windings 44 extend up to the impeller-side end 420 of the posts 40. This has the advantage that a magnetomotive force can be generated along the complete post 40. The magnetic core 400 comprises a protrusion 401 at the rear end 450 of the posts 40 protruding radially in respect to the posts 40. This protrusion 401 can be a stop for the coil windings 44 towards the back plate 50. As the integral magnetic core 400 has a high rigidity between the back plate 50 and the posts 40, a spacer between the posts 40 at the impeller-side end 420 of the posts may be omitted. The integral magnetic core 400 provides the advantage that an optimum magnetic connection between the posts 40 and the back plate 50 can be achieved. The magnetic core 400 may have a diameter of less than 10 mm.

Figures 3A, 3B, 3C:
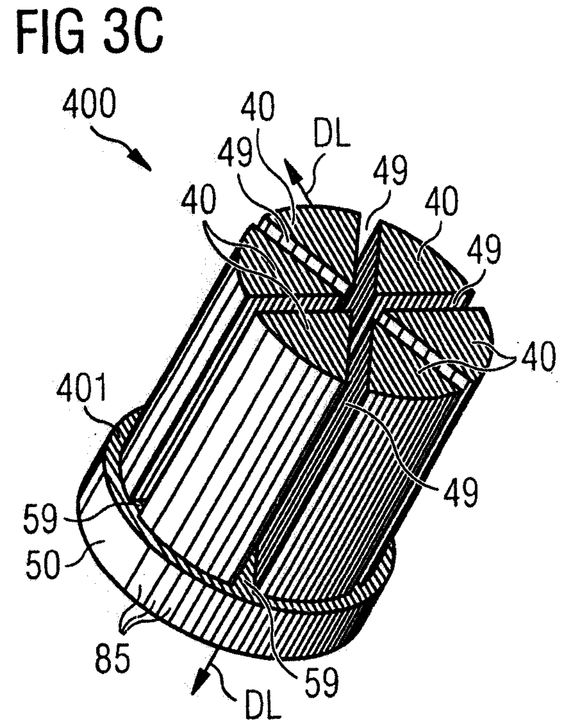
FIGS. 3A to 3C show steps of manufacturing an integrated magnetic core for the drive unit according to FIG. 2.

FIGS. 3A to 3C show steps of manufacturing the magnetic core 400 for the drive unit 4 of the drive unit-impeller-arrangement as shown in FIG. 2. FIG. 3A shows in a perspective view a monoblock 9 in cubical shape which forms a work piece for manufacturing the magnetic core 400. The monoblock 9 consists of a discontinuous soft magnetic material which is discontinuous regarding electrical conductivity. It comprises sheets 85 which are oriented in a direction of lamination DL which runs along the main plane of the sheets 85. The sheets 85 are each bonded to their respective neighbouring sheet by a bonding layer of an electrical non-conductive material, which is not explicitly shown in FIGS. 3A to 3C.

FIG. 3B shows the magnetic core 400 in a semi-manufactured state in which it has been machined, e.g. turned, from the cubical monoblock 9 into a substantially cylindrical body 94. In this machining step, the protrusion 401 is manufactured. A section 404 of reduced diameter of the body 94, which forms a peripheral surface of the posts 40 of the magnetic core 400, is manufactured with a diameter that corresponds to an outer radius of the outermost convex side surfaces 842 of the posts 40.

Then, the body 94 can be further manufactured to produce the magnetic core 400 as shown in FIG. 3C. For this production step, electric discharge machining can be used. Especially electric discharge machining by wire cutting can be applied to produce the slots 49 which separate the posts 40 from each other. Inside the slots, space for the coil windings 44 is provided. At the ground of the slots 49, an intermediate area 59 of the integral back plate 50 extends between the rear ends of the posts 40. The intermediate area is integral with the posts 40 and with the back plate 50. Thus, the whole magnetic core is formed by the monoblock 9.

The direction of lamination DL in the magnetic core 400 is such that it is parallel to the axis of rotation 10. It may be tolerated that the direction of lamination DL in the base plate 50 is not parallel with respect to the magnetic flow between the posts 40 in the base plate 50. It is also possible to manufacture the magnetic core 400 from coiled soft magnetic sheet material which is separated by electrically non-conducting layers. Then, the direction of lamination DL in the base plate 50 is always in the circumferential direction which is advantageous to avoid eddy currents in the magnetic flux in the base plate 50.

Figure 4A:
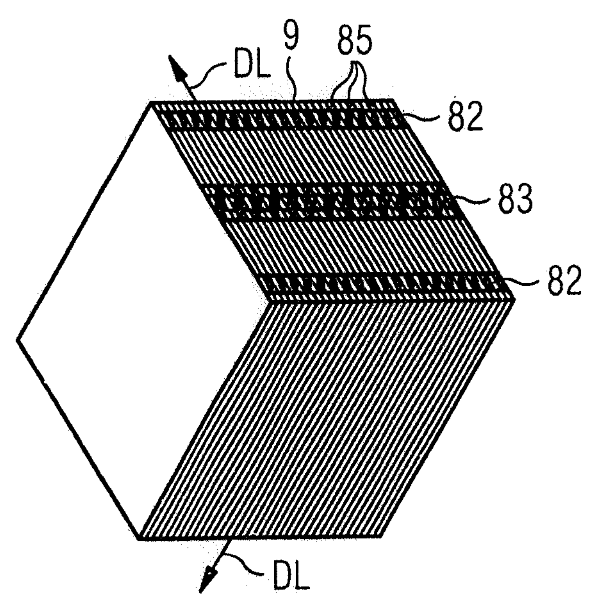
FIGS. 4A to 4C show welds on the integrated magnetic core as manufactured according to FIGS. 3A to 3C.
Figure 4B:
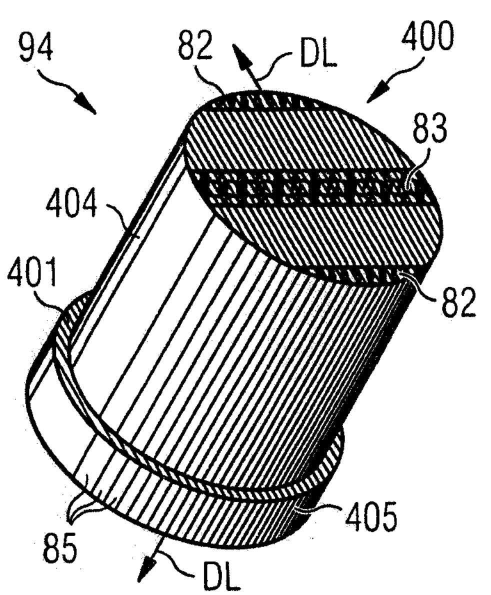
Figure 4C:
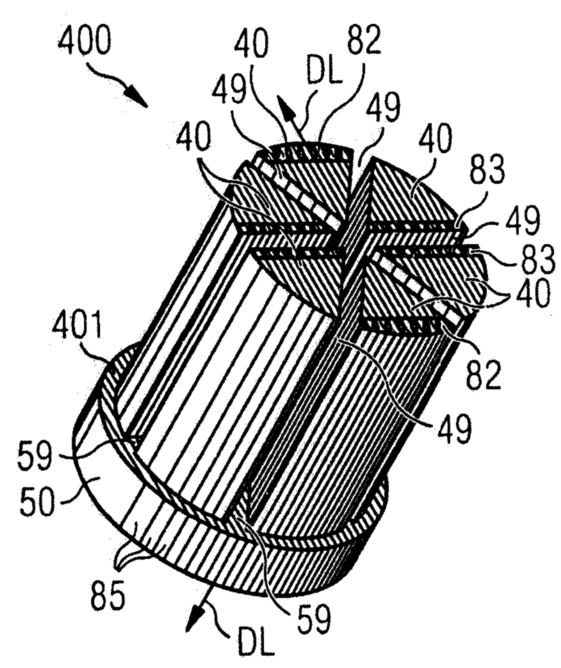

FIGS. 4A to 4C show how one or more welds may be provided on surfaces of the integrated magnetic core as manufactured according to FIGS. 3A to 3C. Accordingly, in the embodiment shown, three weld seams 82, 83 are provided on one side face of the cubical monoblock 9. The weld seams 82, 83 are welded at a distance to each other and across the cross section of the body 94 to be cut out of the monoblock 9. The weld seams 82, 83 run perpendicular to the direction of lamination DL of the sheets 85. In this way, the sheets of the discontinuous soft magnetic material are connected to each other. Instead of three weld seams, more weld seams or a single wide weld may be provided. In addition, similar weld seams may be provided on the opposite side of the monoblock 9 (not shown). Alternatively or in addition to the welds on the opposite side faces, one or more weld seams may be provided on a side surface of the monoblock 9 at the level of the back plate 50 so as to surround the back plate 50 completely or at least partially. The sheets 85 have a better mechanical connection to each other due to the weld seams 82, 83 and are also electrically connected. The latter has the advantage that electrical current can flow from any position of the discontinuous soft magnetic material to each position of electrical connection of the body 94 which may be required e.g. for electric discharge machining. This way, electrical discharge machining is facilitated significantly. Furthermore, higher process reliability is achieved as the back plate-post unit to be cut-out of the body 94 cannot fall apart by delamination. Preferably, laser welding is applied. It may be advantageous to apply welding power to the same weld twice or even more often.

Figure 5E:
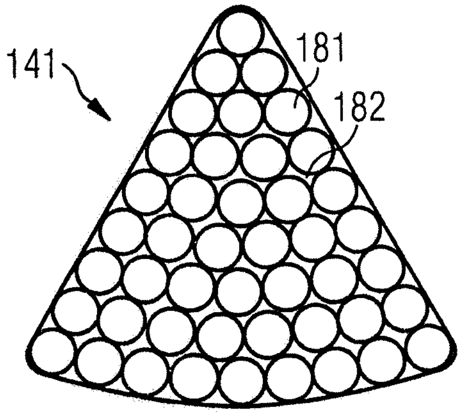

FIGS. 5A to 5J illustrate various embodiments of posts seen in cross section. FIGS. 5A to 5D show embodiments in which the post is slotted, i.e. is formed of a plurality of sheets 171 insulated from each other by insulating layers 172. The insulating layers 172 can comprise adhesive, lacquer, baking enamel or the like. FIGS. 5A and 58 show embodiments in which the thickness of the sheets 171 is uniform. The thickness may be in the range from 25 μm to 450 μm. The sheets 171 shown in FIG. 5A have a greater thickness than the sheets 171 shown in FIG. 5B. The sheets in FIG. 5C have varying thicknesses, with the central sheet having the greatest thickness and the outermost sheets having the smallest thickness. This may be advantageous because eddy currents in the side regions of the posts are more critical and can be reduced by the thin sheets. Eddy currents in the central area are less critical, and the relatively thick central sheet may help in improving the magnetic flux. The orientation of the sheets 171 may be different as exemplarily shown in FIG. 5D as long as the soft magnetic material in the shown cross-section, i.e. the soft magnetic material in cross-section transverse to the direction of the magnetic flux, is discontinuous or interrupted.

Figure 5F:
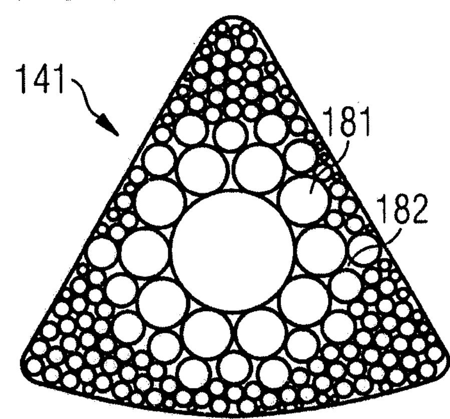
Figure 5G:
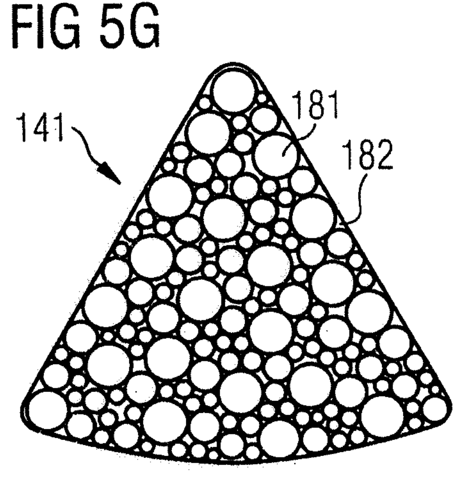
Figure 5H:
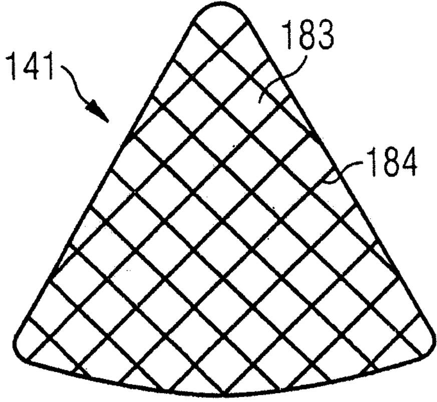

FIGS. 5E and 5F show embodiments in which the posts 141 are formed by a bundle of wires 181 which are insulated from each other by an insulating material 182. The insulating material 182 may be present as a coating of each of the wires 181 or may be a matrix in which the wires 181 are embedded. In the embodiment of FIG. 5E all wires have the same diameter, whereas in the embodiment of FIG. 5F a central wire has a largest diameter and outer wires have smaller diameters, similar to the embodiment shown in FIG. 5C having sheets with varying thicknesses. As shown in FIG. 5G, wires 181 of different diameters may be mixed, which may increase the total cross-sectional area of soft magnetic material compared to embodiments in which all wires have the same diameter. Still alternatively, in order to further minimize insulating layers 184 between the wires 183, the wires 183 may have a polygonal cross-sectional area, such as rectangular, square etc.

Figure 5I:
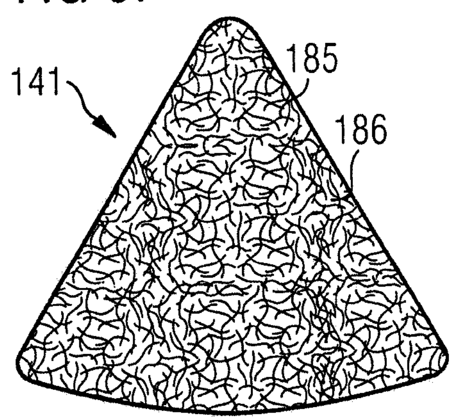
Figure 5J:
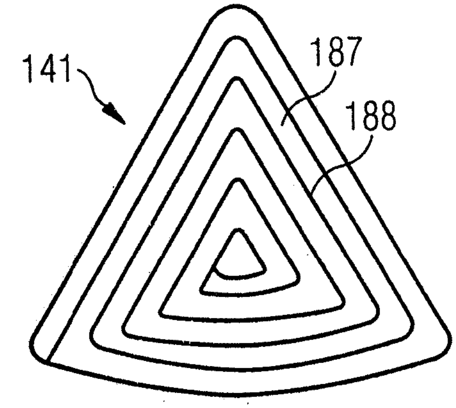

Alternatively, the discontinuous cross-section of the posts 141 may be created by metal particles 185 embedded in a polymer matrix 186 as shown in FIG. 5I, or by steel wool or other porous structures impregnated with an insulating matrix. A porous and, thus, discontinuous structure of soft magnetic material may also be produced by a sintering process or high-pressure molding process, in which an insulating matrix may be omitted because insulating layers are formed automatically by oxidation of the soft magnetic material by exposure to air. Still alternatively, the post 141 may be formed of a rolled-up sheet 187 of a soft magnetic material in which the layers of the rolled-up sheet 187 are separated by insulating layers 188 as shown in FIG. 5J. This also provides a discontinuous cross-section in the sense of the present invention which reduces eddy currents in the posts 141 or the posts 40.

The invention claimed is:

1. An intravascular blood pump for percutaneous insertion into a patient's blood vessel, comprising:

a pump casing having a blood flow inlet and a blood flow outlet, an impeller arranged in said pump casing so as to be rotatable about an axis of rotation, the impeller having blades sized and shaped for conveying blood from the blood flow inlet to the blood flow outlet, a drive unit for rotating the impeller, the drive unit comprising a first end, a second end, and a magnetic core, the magnetic core including a plurality of posts and a back plate, the plurality of posts connected to the back plate, the plurality of posts arranged about the axis of rotation, each of the plurality of posts including a first end and a second end, wherein the back plate is positioned at or near the first end of the drive unit and is connected to the first end of each of the plurality of posts such that each of the plurality of posts extends away from the back plate toward the second end of the drive unit, wherein the back plate further comprises an intermediate area extending between each of the first ends of the plurality of posts, and a plurality of coil windings, each coil winding disposed around a respective one of the plurality of posts, the plurality of coil windings being controllable to create a rotating magnetic field, wherein the impeller comprises a magnetic structure arranged to interact with the rotating magnetic field to cause rotation of the impeller, wherein the plurality of posts and the back plate are defined by a plurality of laminated sheets of soft magnetic material, and at least a portion of at least one sheet of the plurality of laminated sheets extends continuously from within at least one post of the plurality of posts into the back plate and through at least a portion of the intermediate area of the back plate.

2. The intravascular blood pump of claim 1, wherein the plurality of laminated sheets of soft magnetic material form a material that is discontinuous regarding electric conductivity in a cross-section transverse to the axis of rotation.

3. The intravascular blood pump of claim 2, further comprising at least one weld bridging a discontinuity regarding electric conductivity in the material formed by the plurality of laminated sheets of soft magnetic material.

4. The intravascular blood pump of claim 3, wherein at least one of the at least one weld is arranged on a surface of the back plate opposite to the posts.

5. The intravascular blood pump of claim 3, wherein at least one of the at least one weld is arranged on an end surface of a post opposite to the back plate.

6. The intravascular blood pump of claim 1, wherein the plurality of laminated sheets of soft magnetic material are each oriented parallel to each other.

7. The intravascular blood pump of claim 6, wherein the plurality of laminated sheets of soft magnetic material are each oriented parallel to the axis of rotation.

8. The intravascular blood pump of claim 1, wherein the intermediate area of the back plate traverses the axis of rotation.

9. The intravascular blood pump of claim 1, wherein the drive unit and the magnetic structure are disposed in non-overlapping positions with respect to each other along the axis of rotation and the plurality of posts are disposed between the magnetic structure and the back plate.

10. A method of manufacturing a magnetic core for a drive unit of an intravascular blood pump, the magnetic core having an axis of rotation and including a plurality of posts arranged about the axis of rotation and a back plate connecting the plurality of posts, wherein the back plate comprises an intermediate area extending between the plurality of posts, the method comprising the steps of:

providing a monoblock of magnetically conductive material, wherein the monoblock comprises a plurality of laminated sheets of soft magnetic material; and cutting slots into the monoblock to create the plurality of posts and the back plate such that the plurality of posts are arranged about the axis of rotation and the back plate forms one integral piece with the plurality of posts, wherein at least a portion of at least one sheet of the plurality of laminated sheets extends continuously from within at least one post of the plurality of posts into the back plate and through at least a portion of the intermediate area of the back plate.

11. The method of claim 10, wherein the slots are cut using electric discharge machining.

12. The method of claim 11, wherein the slots are cut using wire cutting by electric discharge machining.

13. The method of claim 10, wherein at least one of the slots is cut through the axis of rotation.

14. The method of claim 10, wherein the slots are cut so that the plurality of posts all have an identical length.

15. The method of claim 10, wherein the slots are cut such that the back plate has a thickness which is smaller than a maximum cross-sectional dimension of each of the plurality of posts transverse to a longitudinal axis thereof.

16. The method of claim 10, wherein the slots are cut using electrochemical machining.

17. A method of manufacturing an intravascular blood pump having a drive unit with a magnetic core, wherein the magnetic core is manufactured according to claim 10.

* * * * *